United States Patent
Hirose et al.

(10) Patent No.: US 8,902,432 B2
(45) Date of Patent: Dec. 2, 2014

(54) ADAPTIVE OPTICS APPARATUS AND IMAGING APPARATUS INCLUDING THE SAME

(75) Inventors: Futoshi Hirose, Yokohama (JP); Kenichi Saito, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 427 days.

(21) Appl. No.: 12/907,712

(22) Filed: Oct. 19, 2010

(65) Prior Publication Data

US 2011/0096337 A1 Apr. 28, 2011

(30) Foreign Application Priority Data

Oct. 23, 2009 (JP) ................................. 2009-244948
Feb. 16, 2010 (JP) ................................. 2010-030919

(51) Int. Cl.
| | |
|---|---|
| G01B 9/02 | (2006.01) |
| G02B 26/06 | (2006.01) |
| A61B 3/10 | (2006.01) |
| G01N 21/47 | (2006.01) |
| A61B 3/14 | (2006.01) |
| G01N 21/21 | (2006.01) |
| G01N 21/17 | (2006.01) |

(52) U.S. Cl.
CPC ............... *G02B 26/06* (2013.01); *A61B 3/102* (2013.01); *G01N 21/4795* (2013.01); *A61B 3/14* (2013.01); *G01N 21/21* (2013.01); *G01N 2021/1787* (2013.01); *G01N 2201/0675* (2013.01); *G02F 2203/12* (2013.01); *G02F 2203/18* (2013.01)
USPC .......................................... 356/497; 356/479

(58) Field of Classification Search
USPC ................................ 356/479, 497, 487, 492
See application file for complete search history.

(56) References Cited

U.S. PATENT DOCUMENTS

| | | | | |
|---|---|---|---|---|
| 5,046,824 | A | * | 9/1991 | Pepper ............................ 349/17 |
| 5,068,749 | A | * | 11/1991 | Patel ............................. 349/198 |
| 5,600,440 | A | * | 2/1997 | Bendall ......................... 356/450 |
| 7,367,672 | B2 | | 5/2008 | Akita |
| 7,656,539 | B1 | * | 2/2010 | Lee ............................... 356/521 |
| 2003/0025874 | A1 | | 2/2003 | Williams et al. |
| 2004/0160611 | A1 | * | 8/2004 | Li .................................. 356/521 |
| 2006/0146285 | A1 | | 7/2006 | Hirohara et al. |
| 2007/0013918 | A1 | | 1/2007 | Hauger et al. |

FOREIGN PATENT DOCUMENTS

| | | |
|---|---|---|
| JP | 2001-507258 A | 6/2001 |
| JP | 2004-159784 A | 6/2004 |
| JP | 2007-014569 A | 1/2007 |

(Continued)

OTHER PUBLICATIONS

Patel, Polarization Insensitive Tunable Liquid-Crystal Etalon Filter, pp. 1314-1316, Applied Physics Letter, No. 11, Sep. 1991, XP000232854.

(Continued)

*Primary Examiner* — Tarifur Chowdhury
*Assistant Examiner* — Jonathon Cook
(74) *Attorney, Agent, or Firm* — Canon USA Inc IP Division

(57) ABSTRACT

An adaptive optics apparatus includes a light modulation unit configured to modulate each of two polarization components of light at a position that is optically conjugate to an object, the light being emitted by a light source; and an irradiation unit configured to irradiate the object with light that is modulated by the light modulation unit.

51 Claims, 8 Drawing Sheets

(56) References Cited

FOREIGN PATENT DOCUMENTS

| JP | 2007-515220 A | 6/2007 |
| JP | 2007-183457 A | 7/2007 |
| WO | 03/105678 A2 | 12/2003 |
| WO | 2005/050282 A1 | 6/2005 |
| WO | 2009/054541 A2 | 4/2009 |

OTHER PUBLICATIONS

Restaino et al, Progress Report on the USAF Research Laboratory Liquid Crystal AO Program, pp. 776-781, SPIE vol. 3353, Mar. 1998, XP009144162.

Shemirani et al, Adaptive Compensation of Multimode Fiber Dispersion by Control of Launched Amplitude, Phase, and Polarization, pp. 2627-2639, Journal of Lightwave Technology, vol. 28, No. 18, Sep. 2010, XP011313077.

Sergio R. Restaino et al.,"Progress Report of USAF Research Laboratory Liquid Crystal AO Program", Proc. SPIE, vol. 3353, 776-781, Mar. 1998.

Christian Maurer, Alexander Jesacher, Severin Fürhapter, Stefan Bernet, Monika Ritsch-Marte, Tailoring of Arbitrary Optical Vector Beams, New Journal of Physics, Mar. 30, 2007, vol. 9, article 78, pp. 1-20, IOP Publishing, Bristol, UK, 2007.

* cited by examiner

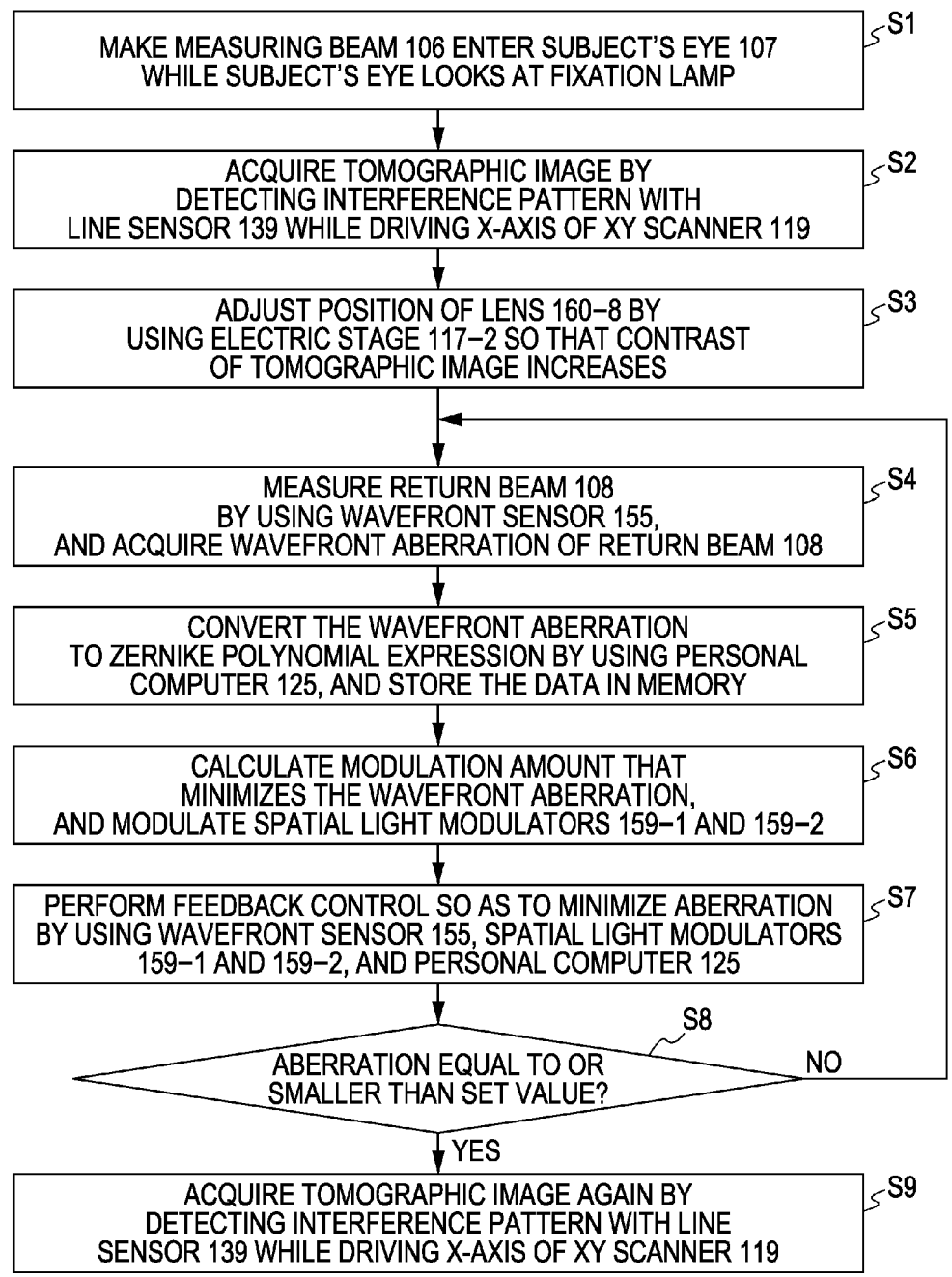

ADAPTIVE OPTICS APPARATUS AND IMAGING APPARATUS INCLUDING THE SAME

BACKGROUND OF THE INVENTION

1. Field of the Invention

The present invention relates to an adaptive optics apparatus and an imaging apparatus including the adaptive optics apparatus.

2. Description of the Related Art

Optical coherence tomography (OCT) using multi-wavelength optical interference is a method of acquiring a high resolution tomographic image of a subject (in particular, an eye ground). Hereinafter, an optical tomographic imaging apparatus that acquires an optical tomographic image by using OCT will be referred to as an OCT apparatus. In recent years, it has become possible to acquire a high-horizontal-resolution tomographic image of a retina by increasing the diameter of the measuring beam used in a Fourier domain OCT apparatus. On the other hand, the increased diameter of the beam diameter of the measuring beam has caused a problem in that, when acquiring a tomographic image of a retina, the signal to noise ratio and the resolution of the tomographic image is decreased due to the aberration generated by the distortion of a curved surface and unevenness of the index of refraction of a subject's eye. To address the problem, an adaptive optics OCT apparatus including an adaptive optics system has been developed. The adaptive optics system measures the aberration of a subject's eye using a wavefront sensor in real time and corrects the aberration using a wavefront correction device, so that a high-horizontal-resolution tomographic image can be acquired.

Japanese Patent Laid-Open No. 2007-14569 describes an ophthalmologic imaging apparatus including such an adaptive optics system. The apparatus is a scanning laser ophthalmoscope (SLO apparatus) that acquires an image of an eye ground by using an adaptive optics system, a liquid crystal spatial phase modulator, a polygon mirror, a galvano mirror, and other components. This ophthalmologic imaging apparatus corrects the aberration generated in a subject's eye by using the liquid crystal spatial phase modulator, thereby preventing the horizontal resolution from decreasing. In general, a liquid crystal spatial phase modulator modulates a specific polarization component aligned with the orientation of liquid crystal and does not modulate other polarization components. Therefore, it is difficult for the ophthalmologic imaging apparatus to correct a polarization component irrespective of the polarization state of reflected light reflected from the eye ground. In this respect, the ophthalmologic imaging apparatus has a room for improvement in acquiring a high-horizontal-resolution image. Regarding a spatial phase modulator for use in an adaptive optics system, "Progress report of USAF Research Laboratory liquid crystal AO program", Proc. SPIE, Vol. 3353, 776 (1998) describes a transmissive liquid crystal spatial phase modulator in which two liquid crystal elements having different liquid-crystal orientations are stacked. This spatial phase modulator can modulate an incident beam irrespective of the polarization state of the incident beam.

SUMMARY OF THE INVENTION

However, the structure in which two liquid crystal elements are stacked has a problem in that it is difficult to disposed the two liquid crystal elements so as to be optically conjugate to each other. As a result, the modulator imposes a limitation on the optical design of an adaptive optics OCT apparatus.

The present invention provides an optical imaging apparatus and an optical imaging method that, by using an adaptive optics system including a spatial light modulation unit, can modulate at least one of a measuring beam and a return beam irrespective of the polarization state and can increase the signal to noise ratio of an optical image by correcting the aberration.

According to an aspect of the present invention, an adaptive optics apparatus includes a light modulation unit configured to modulate each of two polarization components of light at a position that is optically conjugate to an object, the light being emitted by a light source; and an irradiation unit configured to irradiate the object with light that is modulated by the light modulation unit.

According to the present invention, an optical imaging apparatus and an optical imaging method that, by using an adaptive optics system including a spatial light modulation unit, can modulate at least one of a measuring beam and a return beam irrespective of the polarization state and can increase the signal to noise ratio of an optical image by correcting the aberration can be realized.

Further features of the present invention will become apparent from the following description of exemplary embodiments with reference to the attached drawings.

BRIEF DESCRIPTION OF THE DRAWINGS

FIG. 3 is a flowchart illustrating steps of acquiring a tomographic image by using the OCT apparatus according to the first embodiment of the present invention.

DESCRIPTION OF THE EMBODIMENTS

Hereinafter, embodiments of the present invention will be described with reference to the drawings. Here, an optical imaging apparatus that is an OCT apparatus that acquires an image of a subject's eye will be described. However, the present invention can be applied to other optical imaging apparatuses such as a scanning laser ophthalmoscope (SLO apparatus).

First Embodiment

An OCT apparatus according to a first embodiment of the present invention will be described. In particular, in the first embodiment, an OCT apparatus including an adaptive optics system that acquires a tomographic image (OCT image) of a subject's eye with high horizontal resolution will be described. The first embodiment is a Fourier domain OCT apparatus that corrects the aberration of the subject's eye by using two reflective spatial light modulators and acquires a tomographic image of a subject's eye. Such an OCT apparatus can acquire a good tomographic image irrespective of the diopter or the aberration the subject's eye. The two reflective spatial light modulators are parallely disposed in the OCT apparatus. Here, the spatial light modulators are reflective liquid crystal spatial phase modulators that employ the orientation of liquid crystal. As long as the spatial light modulators can modulate the phase of light, materials other than liquid crystal may be used.

Figure 1A:
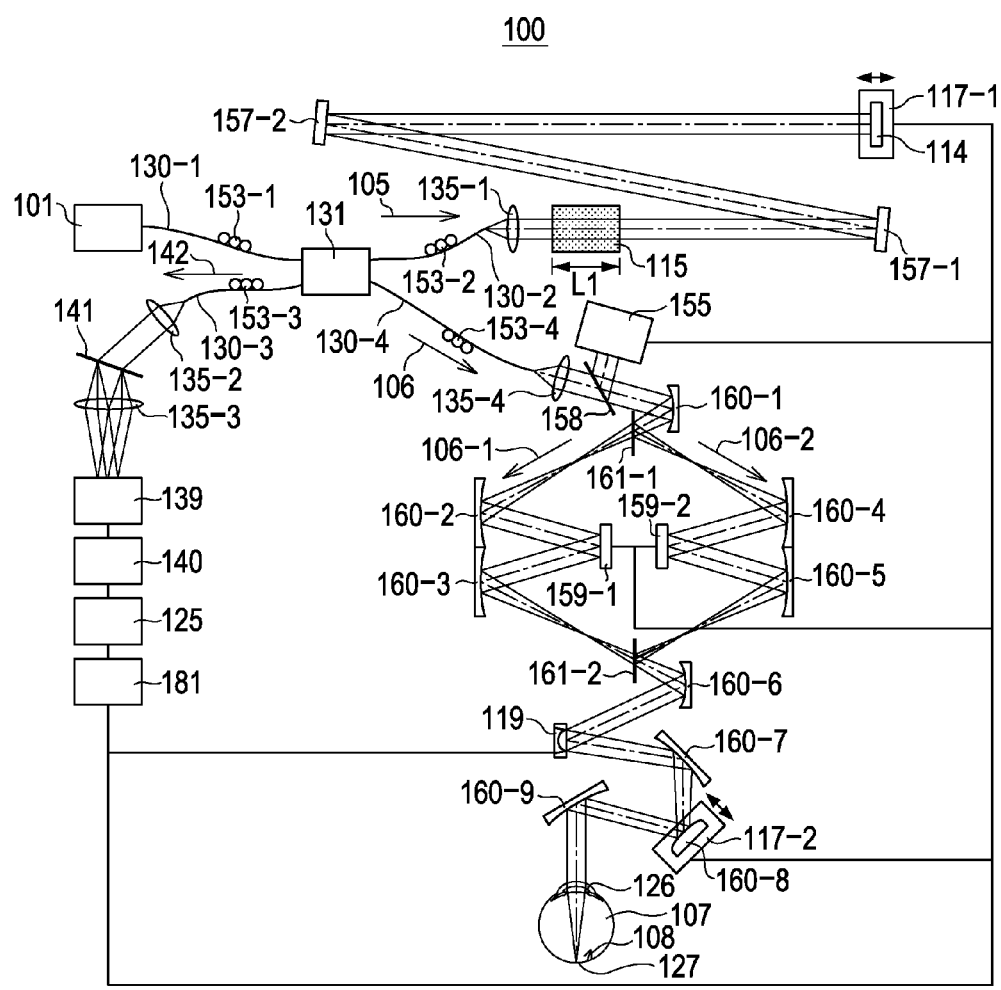
FIGS. 1A to 1C illustrate the overall structure of an OCT apparatus according to a first embodiment of the present invention.

Referring to FIG. 1A, the overall structure of the OCT apparatus according to the first embodiment will be described. As illustrated in FIG. 1A, the entirety of an OCT apparatus 100 according to the first embodiment is a Michelson interferometer system. In FIG. 1A, a beam is emitted by a light source 101, and the beam travels through an optical fiber 130-1 and an optical coupler 131, where the beam is split into a reference beam 105 and a measuring beam 106 with a ratio of 90:10. The measuring beam 106 travels through an optical fiber 130-4, two spatial light modulators 159-1 and 159-2 that are parallely disposed, an XY scanner 119, and spherical mirrors 160-1 to 160-9, and reaches a subject's eye 107 that is an object to be observed.

The measuring beam 106 is reflected or scattered by the subject's eye 107, which is an object to be observed, and returned as a return beam 108. The return beam 108 is combined with the reference beam 105 by the optical coupler 131. Polarization controllers 153-1 to 153-4 adjust the polarization states of the measuring beam 106 and the reference beam 105. The reference beam 105 and the return beam 108 are combined and then split into wavelength components by a transmissive grating 141 and enter a line sensor 139. The line sensor 139 converts the intensity of light at each position (wavelength) to a voltage signal. A personal computer 125 generates a tomographic image of the subject's eye 107 by using the voltage signal. An electric stage 117, the XY scanner 119, and the spatial light modulators 159-1 and 159-2 are driven by a driver unit 181 that is controlled by the personal computer 125. The aberration of the return beam 108 is measured by a wavefront sensor 155. The two spatial light modulators 159-1 and 159-2, which are parallely disposed, are controlled so as to reduce the aberration and so as to obtain a good tomographic image irrespective of the diopter or the aberration of the subject's eye. The optical system of the first embodiment is a reflective optical system using spherical mirrors as the main components. However, the optical system may be a refractive optical system using lenses instead of the spherical mirrors. In the first embodiment, reflective spatial light modulators are used. However, transmissive spatial light modulators may be used.

Next, the light source 101 will be described. The light source 101 is a super luminescent diode (SLD), which is a typical low-coherence light source, having a wavelength of 830 nm and a bandwidth of 50 nm. The bandwidth is an important parameter that affects the resolution of an acquired tomographic image in the optical axis direction. Here, the light source is the SLD. However, other light sources, such as an amplified spontaneous emission (ASE) device or the like can be used, as long as low-coherence light can be emitted. Using near infrared light is appropriate for measuring an eye. A shorter wavelength is more appropriate, because the wavelength affects the horizontal resolution of an acquired tomographic image. In the first embodiment, the wavelength is 830 nm. The wavelength may be different from this in accordance with the position of the object to be measured.

Next, the optical path of the reference beam 105 will be described. The reference beam 105, which has been split by the optical coupler 131, travels through a single mode fiber 130-2 to a lens 135-1 that collimates the reference beam 105 into a collimated beam having a diameter of 4 mm. Next, the reference beam 105 is reflected by mirrors 157-1 and 157-2 to a mirror 114, which is a reference mirror. The optical path length of the reference beam 105 is made substantially the same as the optical path length of the measuring beam 106, so that the reference beam 105 can interfere with the measuring beam 106. Next, the reference beam 105 is reflected by the mirror 114, and guided again to the optical coupler 131. The reference beam 105 passes through a dispersion compensation glass 115 that compensates the reference beam 105 for the dispersion that is generated while the measuring beam 106 travels to and returns from the subject's eye 107. The dispersion compensation glass 115 has a length L1. Here, L1=23 mm, which corresponds to the diameter of an eyeball of an average Japanese person. An electric stage 117-1 can move in a direction indicated by an arrow so as to adjust the optical path length of the reference beam 105. The electric stage 117-1 is driven by an electric stage driver of the driver unit 181 that is controlled by the personal computer 125.

Next, the optical path of the measuring beam 106, which characterizes the first embodiment, will be described. The measuring beam 106, which has been split by the optical coupler 131, is guided through the optical fiber 130-4 to a lens 135-4 that collimates the measuring beam 106 into a collimated beam having a diameter of 4 mm. The polarization controller 153-1 or 153-4 can adjust the polarization state of the measuring beam 106. Here, the polarization state of the measuring beam 106 can be circular polarized. The measuring beam 106 passes through a beam splitter 158, is reflected by the spherical mirror 160-1, and enters a first polarizing beam splitter 161-1. The measuring beam 106 is split into a first measuring beam 106-1 that is a p-polarization component and a second measuring beam 106-2 that is an s-polarization component. The first measuring beam 106-1 is reflected by the spherical mirror 160-2, modulated by the first spatial light modulator 159-1, reflected by the spherical mirror 160-3, and enters a second polarizing beam splitter 161-2 that is disposed nearer to the object than the spherical mirror 160-3. The first spatial light modulator 159-1 is oriented so as to modulate the phase of p-polarized light.

The second measuring beam 106-2 is reflected by the spherical mirror 160-4, modulated by the second spatial light modulator 159-2, reflected by the spherical mirror 160-5, and enters the second polarizing beam splitter 161-2. The second spatial light modulator 159-2 is oriented so as to modulate the phase of s-polarized light. The spatial light modulators 159-1 and 159-2 each modulate a polarization component having a specific polarization direction by employing the orientation of liquid crystal. Therefore, the first embodiment can modulate the measuring beam 106 irrespective of the polarization state of the measuring beam 106 by splitting the measuring beam 106 into s-polarized light and p-polarized light and performing modulation by using the first spatial light modulator 159-1 and the second spatial light modulator 159-2. As described above, the orientations of the liquid crystal of the spatial light modulators 159-1 and 159-2 can be perpendicular to each other. However, in practice, the orientations may not be perpendicular to each other, as long as the orientations are not the same.

Next, the first measuring beam 106-1 and the second measuring beam 106-2 are combined into the measuring beam 106 by the second polarizing beam splitter 161-2. The measuring beam 106 is reflected by the spherical mirror 160-6, and impinges on a mirror of the XY scanner 119. For simplicity, the XY scanner 119 is illustrated as a mirror. In practice, however, an X-scanning mirror and a Y-scanning mirror are disposed adjacent to each other so as to raster scan a retina 127 in a direction perpendicular to the optical axis. The center of the measuring beam 106 is aligned with the center of the rotation center of the mirror of the XY scanner 119. The spherical mirrors 160-7 to 160-9, which serve as an optical system for scanning the retina 127, make the measuring beam 106 scan the retina 127 with a point near a cornea 126 as a fulcrum. Here, the beam diameter of the measuring beam 106 is 4 mm. In order to acquire a tomographic image having a higher resolution, the beam diameter may be larger. An electric stage 117-2 can move in a direction indicated by an arrow so as to adjust the position of a spherical mirror 160-8 attached thereto. By adjusting the position of the spherical mirror 160-8, the measuring beam 106 can be focused on a predetermined layer of the retina 127 of the subject's eye 107 so as to observe the layer. Even when the subject's eye 107 has ametropia, the subject's eye can be observed. After entering the subject's eye 107, the measuring beam 106 is reflected or scattered by the retina 127 to become the return beam 108, is guided again to the optical coupler 131, and reaches the line sensor 139. The return beam 108 is split into s-polarized light and p-polarized light by the polarizing beam splitter 161-2. The s-polarized light and p-polarized light are respectively modulated by the spatial light modulators 159-1 and 159-2 and combined by the polarizing beam splitter 161-1.

A part of the return beam 108, which is split from the return beam 108 by the beam splitter 158, enters the wavefront sensor (aberration measuring unit) 155, which measures the aberration of the return beam 108 that is generated in the subject's eye 107. Here, the OCT apparatus 100 includes one wavefront sensor 155. However, two wavefront sensors may be used to measure the aberration for each of the polarized light. This will be described below in detail in the second embodiment. The wavefront sensor 155 is electrically connected to the personal computer 125.

Here, the spherical mirrors 160-1 to 160-9 are disposed so that the cornea 126, the XY scanner 119, the wavefront sensor 155, and the spatial light modulators 159-1 and 159-2 are optically conjugate to each other. Therefore, the wavefront sensor 155 can measure the aberration of the subject's eye 107. Moreover, the spatial light modulators 159-1 and 159-2 can correct the aberration due to the subject's eye 107. Furthermore, the spatial light modulators 159-1 and 159-2 are controlled in real time on the basis of the aberration measured by the wavefront sensor 155, so that the aberration generated in the subject's eye 107 is corrected and a tomographic image having a higher horizontal resolution can be acquired.

Figure 1B:
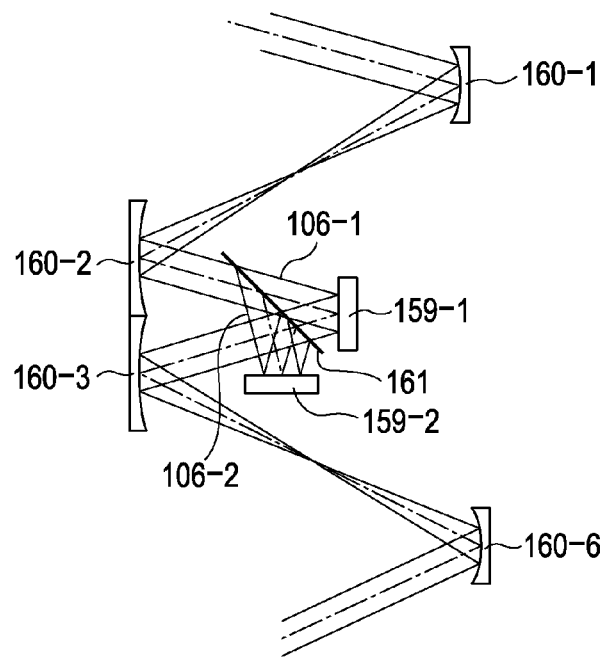

Instead of the spherical mirror 160-8 used here, a cylindrical mirror may be used depending on the aberration (ametropia) of the subject's eye 107. An additional lens may be disposed on the optical path of the measuring beam 106. Here, the wavefront sensor 155 measures the aberration by using the measuring beam 106. However, the aberration may be measured by using an aberration measuring beam that is emitted by another light source. An additional optical path may be made in order to measure the aberration. For example, a beam splitter may be disposed between the spherical mirror 160-9 and the cornea 126 so as to generate a beam for measuring the aberration. Here, after the measuring beam 106 is reflected by the spherical mirror 160-1, the measuring beam 106 is split by the polarizing beam splitter 161-1 into the first measuring beam 106-1 that is p-polarized and the second measuring beam 106-2 that is s-polarized. However, the measuring beam 106 may be split at another position so as to make a measuring optical path. For example, as illustrated in FIG. 1B, after the measuring beam 106 is reflected by the spherical mirror 160-2, the measuring beam 106 can be split by a polarizing beam splitter 161 into the first measuring beam 106-1 that is p-polarized and second measuring beam 106-2 that is s-polarized. Here, the first measuring beam 106-1 is modulated by the first spatial light modulator 159-1, passes through the polarizing beam splitter 161, and impinges on the spherical mirror 160-3. Likewise, the second measuring beam 106-2 is modulated by the second spatial light modulator 159-2, reflected by the polarizing beam splitter 161, and impinges on the spherical mirror 160-3. Thus, the polarizing beam splitter 161 performs functions of the polarizing beam splitter 161-1 and the polarizing beam splitter 161-2.

Next, the structure of the measurement system of the OCT apparatus according to the first embodiment will be described. The OCT apparatus 100 can acquire a tomographic image (OCT image) that is formed of the intensity of an interference signal measured by a Michelson interferometer system. In the measurement system, the return beam 108, which has been reflected or scattered by the retina 127, is guided through the lens 135-4 and the optical fiber 130-4 to the optical coupler 131, which combines the return beam 108 with the reference beam 105 to generate a combined beam 142. The combined beam 142 travels through an optical fiber 130-3 and a lens 135-2 and enters the transmissive grating 141. The combined beam 142 is split into wavelength components by the transmissive grating 141, focused by a lens 135-3, and the line sensor 139 converts the intensity of the combined beam at each position (wavelength) to a voltage. To be specific, an interference pattern of spectral regions on the wavelength axis is observed on the line sensor 139.

The voltage signals that have been acquired are converted to digital data by a frame grabber 140. The personal computer 125 performs data processing and generates a tomographic image. Here, the line sensor 139 has 1024 pixels and can acquire the intensity of each of the wavelengths (1024 wavelength segments) of the combined beam 142. A part of the return beam 108, which is split by the beam splitter 158, enters the wavefront sensor 155, and the aberration of the return beam 108 is measured. The wavefront sensor 155 is a Shack-Hartmann wavefront sensor. An image signal acquired by the wavefront sensor 155 is input to the personal computer 125, and the aberration is calculated. The aberration is represented by using a Zernike polynomial, which represents the aberration of the subject's eye 107. The Zernike polynomial includes tilt terms, defocus terms, astigmatism terms, coma terms, trefoil terms, etc.

Figure 1C:
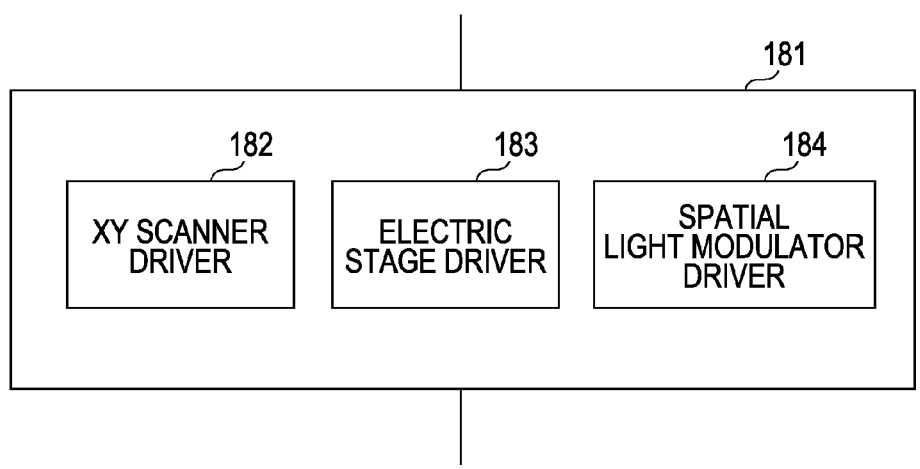
Figure 2A:
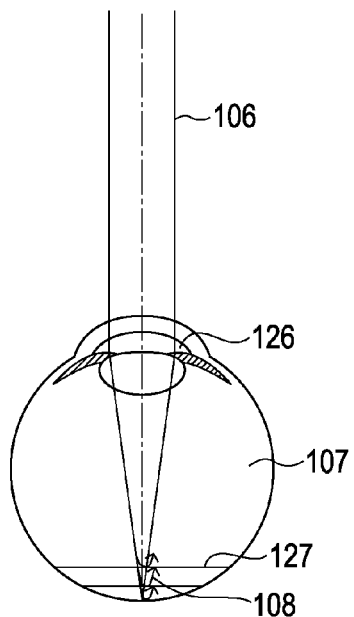
FIGS. 2A to 2C illustrate a method of acquiring a tomographic image by using the OCT apparatus according to the first embodiment of the present invention.
Figure 2B:
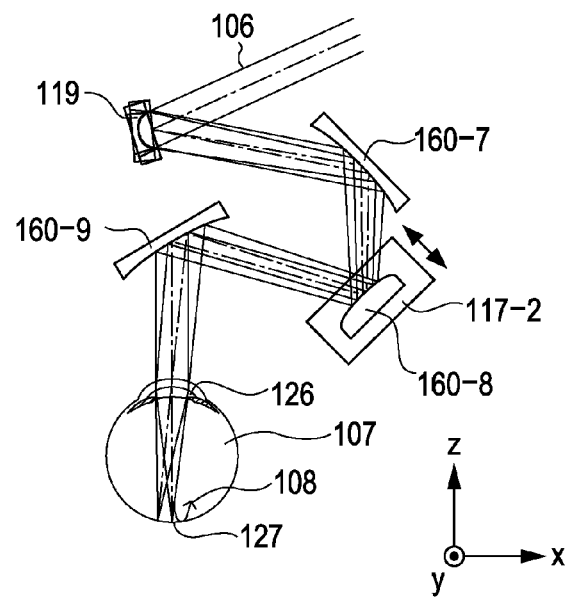
Figure 2C:
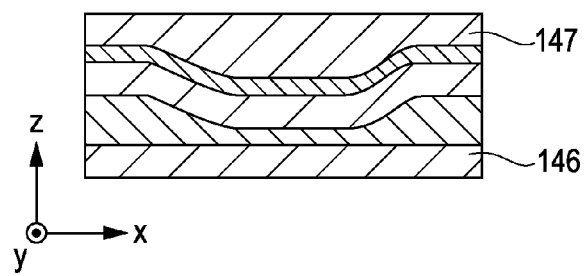

Next, a method of acquiring a tomographic image by using the OCT apparatus will be described. The OCT apparatus 100 can acquire a tomographic image of the retina 127 by controlling the XY scanner 119 and acquiring an interference pattern with the line sensor 139 (FIGS. 1A to 1C). The XY scanner 119 is driven by an XY scanner driver 182 of the driver unit 181 (FIG. 1C) that is controlled by the personal computer 125. Referring to FIGS. 2A to 2C, a method of acquiring a tomographic image (in a plane parallel to the optical axis) of the retina 127 will be described. FIG. 2A is a schematic view of the subject's eye 107, which is being observed by the OCT apparatus 100. As illustrated in FIG. 2A, the measuring beam 106 passes through the cornea 126 and enters the retina 127. In the retina 127, the measuring beam 106 is reflected and scattered at various positions and becomes the return beam 108. The return beam 108, which has been delayed at the various positions, reaches the line sensor 139. Here, the light source 101 has a wide bandwidth and a short coherence length. Therefore, the line sensor 139 can detect an interference pattern in the case where the optical path length of the reference optical path is substantially equal to the optical path length of the measuring optical path. As described above, the line sensor 139 acquires an interference pattern of spectral regions on the wavelength axis. Next, the interference pattern, which is the information along the wavelength axis, is converted to an interference pattern on an optical frequency axis with consideration of the characteristics of the line sensor 139 and the transmissive grating 141. The interference pattern on the optical frequency axis is inverse Fourier transformed to acquire the information in the depth direction.

As illustrated in FIG. 2B, by detecting the interference pattern while driving the X-axis of the XY scanner 119, the interference pattern for each position on the X-axis is acquired, i.e., the information in the depth direction for each position on the X-axis can be acquired. As a result, a two-dimensional distribution of the intensity of the return beam 108 in the XZ-plane, which is a tomographic image 132 (FIG. 2C), is acquired. In practice, the tomographic image 132 is the arrayed intensities of the return beam 108, and displayed, for example, by representing the intensities in gray scale. Here, only the boundaries of the acquired tomographic image are illustrated. A pigmented layer 146 and an optic nerve fiber layer 147 of the retina are illustrated.

Referring to FIGS. 1A to 3, the steps of acquiring a tomographic image by using the OCT apparatus will be described. FIG. 3 is a flowchart illustrating the steps of acquiring a tomographic image by using the OCT apparatus 100. Here, as illustrated in FIGS. 1A to 1C, an aberration generated in the subject's eye 107 having myopia and astigmatism is corrected by using the two spatial light modulators 159-1 and 159-2 so as to acquire a high-horizontal-resolution tomographic image of the retina 127. Needless to say, the same method can be used in the case where the subject's eye 107 has only myopia or hyperopia. The tomographic image is acquired by performing the following steps (1) to (9). The steps may be performed sequentially or in a different order. The steps may be automatically performed by using a computer or the like. FIG. 3 is a flowchart of the process of acquiring the tomographic image.

(1) In step 1 (S1 in FIG. 3), the measuring beam 106 is made to enter the subject's eye 107 while the subject's eye 107 looks at a fixation lamp (not shown). Here, the position of the spherical mirror 160-8 is adjusted by the electric stage 117-2 so that the measuring beam 106 enters the subject's eye 107 as a collimated beam.

(2) In step 2 (S2 in FIG. 3), a tomographic image (not shown) is acquired by detecting an interference pattern with the line sensor 139 while driving the X-axis of the XY scanner 119.

(3) In step 3 (S3 in FIG. 3), while performing step 2, the position of the spherical mirror 160-8 is adjusted by using the electric stage 117-2 so that the contrast of the tomographic image increases.

(4) In step 4 (S4 in FIG. 3), the return beam 108 is measured by using the wavefront sensor 155, and the aberration of the return beam 108 is acquired.

(5) In step 5 (S5 in FIG. 3), the acquired aberration is converted to a Zernike polynomial expression by using the personal computer 125, and the data is stored in a memory.

(6) In step 6 (S6 in FIG. 3), a modulation amount that minimizes the acquired aberration is calculated, and the spatial light modulators 159-1 and 159-2 are modulated. Here, because the first spatial light modulator 159-1 and the second spatial light modulator 159-2 are optically conjugate to each other, the same modulation amount is input to the spatial light modulators 159-1 and 159-2.

(7) In step 7 (S7 in FIG. 3), feedback control is performed so as to minimize the aberration by using the wavefront sensor 155, the spatial light modulators 159-1 and 159-2, the personal computer 125, and a spatial light modulator driver 184 so as to control the spatial light modulators 159-1 and 159-2 in real time.

(8) In step 8 (S8 in FIG. 3), whether the aberration is equal to or smaller than a set value is determined, and steps 4 to 7 are repeated until the aberration converges. The set value can be about 0.1 µm (root mean square (RMS)).

(9) In step 9 (S9 in FIG. 3), while driving the X-axis of the XY scanner 119, the interference pattern is detected by using the line sensor 139, and a tomographic image is obtained again.

As described above, with the structure according to the first embodiment including the spatial light modulator, at least one of the measuring beam and the return beam can be modulated and the aberration can be corrected irrespective of the polarization state. The return beam, which has a small amount of aberration, can be coupled to an optical fiber with high efficiency, and thereby the signal to noise ratio of the tomographic image can be increased. The spatial light modulator and the wavefront sensor are disposed optically conjugate to each other, so that the aberration can be efficiently corrected. The spatial light modulator includes the first spatial light modulator and the second spatial light modulator, so that the spatial light modulator can modulate a plurality of different polarization components and efficiently increase the signal to noise ratio. The first spatial light modulator and the second spatial light modulator are spatial light modulators employing the orientation of liquid crystal, and the first spatial light modulator and the second spatial light modulator optically parallely disposed on the optical path from the light source to an object, whereby the signal to noise ratio can be increased. That is, the number of times the measuring beam or the return beam passes through the spatial light modulator can be minimized, so that the loss in the amount of light due to the spatial light modulator can be reduced, whereby the signal to noise ratio of the tomographic image can be increased. The first polarizing beam splitter and the second polarizing beam splitter are disposed so as to split the measuring beam into polarization components that are different from each other and so as to combine the measuring beam that has been split into polarization components that are different from each other, whereby the signal to noise ratio can be increased. That is, the measuring beam and the return beam can be efficiently guided to the spatial light modulator, and the loss in the amount of light in the spatial light modulator can be reduced, whereby the signal to noise ratio of the tomographic image can be increased. One polarizing beam splitter splits and combines the measuring beam, so that an optical tomographic imaging apparatus including a small optical system can be realized. The orientations of liquid crystal in the first spatial light modulator and the second spatial light modulator are perpendicular to each other, so that the measuring beam or the return beam can be efficiently modulated irrespective of the polarization state. The modulation amounts of the first spatial light modulator and the second spatial light modulator are the same, so that an optical tomographic imaging apparatus having a simple structure can be realized.

Moreover, in the first embodiment, light emitted from the light source is split into the measuring beam and the reference beam, and by using an interference signal generated by the interference between the return beam of the measuring beam, with which the object is irradiated, and the reference beam, which has traveled through the reference optical path, an optical imaging method of acquiring a tomographic image of the object can be constructed. Thus, the measuring beam or the return beam can be modulated and the aberration can be corrected irrespective of the polarization state. As a result, the signal to noise ratio of the tomographic image can be increased.

Second Embodiment

An OCT apparatus according to a second embodiment of the present invention will be described. In particular, an OCT apparatus including an adaptive optics system that acquires a high horizontal resolution tomographic image (OCT image) of a subject's eye will be described. The second embodiment is a Fourier domain OCT apparatus that acquires a tomographic image of a subject's eye by correcting the aberration of the subject's eye by using two reflective spatial light modulators. Using the OCT apparatus a good tomographic image can be acquired irrespective of the diopter or the aberration of the subject's eye. Here, the two reflective spatial light modulators are serially disposed. Two wavefront sensors are used to measure the aberration for each polarized beam. First, referring to FIG. 4, the overall structure of the optical system of the OCT apparatus according to the second embodiment will be described. In the second embodiment, the elements the same as those of FIGS. 1A to 1C are denoted by the same numerals, and redundant description will be omitted.

Figure 4:
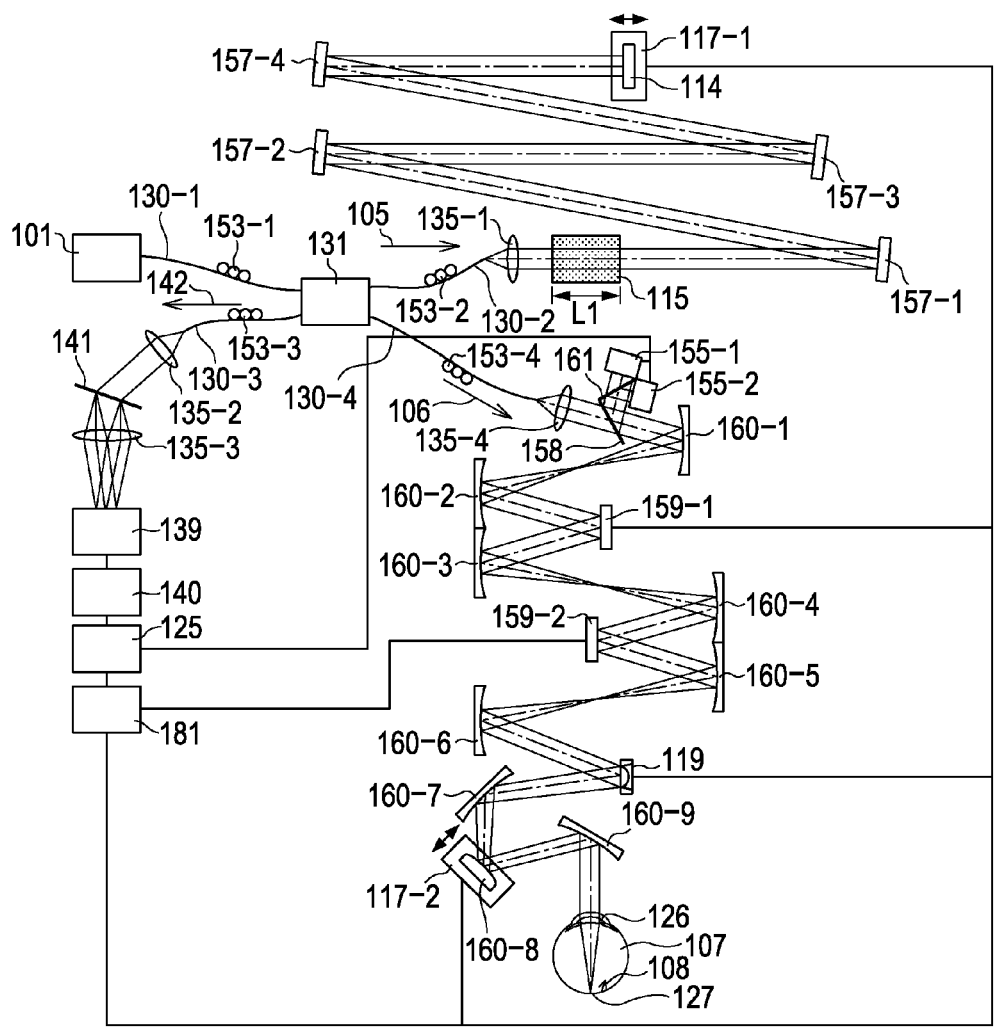
FIG. 4 illustrates the overall structure of an OCT apparatus according to a second embodiment of the present invention.

In FIG. 4, the measuring beam 106 is guided through the optical fiber 130-4, two spatial light modulators 159-1 and 159-2 that are serially disposed, the XY scanner 119, and the spherical mirrors 160-1 to 9, to the subject's eye 107, which is an object to be observed. The aberration of the return beam 108 is measured by wavefront sensors 155-1 and 155-2. The two spatial light modulators 159-1 and 159-2, which are serially disposed, are controlled so as to reduce the aberration, so that a good tomographic image can be obtained irrespective of the diopter or the aberration of the subject's eye. The optical system of the second embodiment is a reflective optical system using spherical mirrors as the main components. However, the optical system may be a refractive optical system using lenses instead of the spherical mirrors. In the first embodiment reflective spatial light modulators are used. However, transmissive spatial light modulators may be used. The description of the light source 101, which is the same as that of the first embodiment, is omitted. The reference beam 105 is guided to the mirror 114, which is a reference mirror, by the mirrors 157-1 to 157-4.

Next, the optical path of the measuring beam 106, which characterizes the second embodiment, will be described. The measuring beam 106 passes through the beam splitter 158, is reflected by the spherical mirrors 160-1 and 160-2, and enters the first spatial light modulator 159-1. Here, the first spatial light modulator 159-1 is oriented so as to modulate the phase of p-polarized light. Next, the measuring beam 106 is modulated by the first spatial light modulator 159-1, reflected by the spherical mirrors 160-3 and 160-4, and enters the second spatial light modulator 159-2. Here, the second spatial light modulator 159-2 is oriented so as to modulate the phase of s-polarized light. The spatial light modulators 159-1 and 159-2 each modulate a polarization component having a specific polarization direction by employing the orientation of liquid crystal. Therefore, as described above, the second embodiment can modulate all polarization components of the measuring beam 106 by continuously performing modulation on the p-polarization component and the s-polarization component of the measuring beam 106. As described above, the orientations of the of the liquid crystal of the spatial light modulators 159-1 and 159-2 can be perpendicular to each other. However, in practice, the orientations may not be perpendicular to each other, as long as the orientations are not the same.

Next, the measuring beam 106 is modulated by the second spatial light modulator 159-2, reflected by the spherical mirrors 160-5 and 160-6, and enters the mirror of the XY scanner 119. The s-polarization component and the p-polarization component of the return beam 108 are respectively modulated again by the second spatial light modulator 159-2 and the first spatial light modulator 159-1. A part of the return beam 108, which is split from the return beam 108 by the beam splitter 158, enters the wavefront sensors (aberration measuring units) 155-1 and 155-2 that measure the aberration of the return beam 108. Here, the return beam 108 is split into the -polarization component and the s-polarization component by the polarizing beam splitter 161. As a result, the wavefront sensors 155-1 and 155-2 detect the p-polarization component and the s-polarization component of the return beam 108. Here, two wavefront sensors 155-1 and 155-2 are used. However, as in the first embodiment, one wavefront sensor 155 may be used. The wavefront sensors 155-1 and 155-2 are electrically connected to the personal computer 125.

Here, the spherical mirrors 160-1 to 160-9 are disposed so that the cornea 126, the XY scanner 119, the wavefront sensor 155, and the spatial light modulators 159-1 and 159-2 are optically conjugate to each other. Therefore, the wavefront sensors 155-1 and 155-2 can measure the aberration of the subject's eye 107. Moreover, the spatial light modulators 159-1 and 159-2 can correct the aberration of the subject's eye 107. Furthermore, the spatial light modulators 159-1 and 159-2 are controlled in real time on the basis of the aberration measured by the wavefront sensor, so that the aberration generated in the subject's eye 107 is corrected and a tomographic image having a higher horizontal resolution can be acquired.

Furthermore, the spatial light modulator 159-1 is controlled on the basis of the aberration of the p-polarization component of the return beam 108 acquired by the wavefront sensor 155-1, only the p-polarization component of the aberration generated in the subject's eye 107 can be corrected. Likewise, the spatial light modulator 159-2 is controlled on the basis of the aberration of the s-polarization component of the return beam 108 acquired by the wavefront sensor 155-2, only the s-polarization component of the aberration generated in the subject's eye 107 can be corrected. As a result, the aberration for each polarization component and controlling the spatial light modulators 159-1 and 159-2 are measured, so that the aberration generated in the subject's eye 107 can be corrected and a tomographic image having a higher horizontal resolution can be acquired. In particular, the aberration can be efficiently corrected when the aberration generated in the subject's eye 107 is polarization-dependent. The descriptions of the structure of the measurement system and the method of acquiring a tomographic image, which are the same as those of the first embodiment, are omitted. The description of the steps of acquiring a tomographic image, which are the same as those of the first embodiment, is omitted.

As described above, the first spatial light modulator and the second spatial light modulator are optically serially disposed on the optical path from the light source to the object, so that the optical tomographic imaging apparatus having a simply-structured optical path can be realized. The first wavefront sensor and the second wavefront sensor measure the polarization components that are different from each other, so that the aberration for each polarization component can be measured and the aberration that is generated in the subject's eye for each polarization component can be corrected. As a result, the aberration generated in the subject's eye can be efficiently corrected when the aberration is polarization-dependent. The first wavefront sensor measures the polarization component that has the same polarization as the polarization component modulated by the first spatial light modulator and the second wavefront sensor measures the polarization component that has the same polarization as the polarization component modulated by the second spatial light modulator, so that the aberration generated in the subject's eye for each polarization component can be corrected. That is, measurement and modulation can be performed on each polarization component measure, whereby the aberration generated in the subject's eye for each polarization component can be corrected. As a result, the aberration can be efficiently corrected when the aberration generated in the subject's eye is polarization-dependent. The first spatial light modulator is modulated on the basis of the aberration acquired by the first wavefront sensor, and the second spatial light modulator is modulated on the basis of the aberration acquired by the second wavefront sensor, whereby the aberration can be efficiently corrected. That is, measurement and modulation can be performed on each polarization component measure, whereby the aberration generated in the subject's eye for each polarization component can be corrected. As a result, the aberration can be efficiently corrected when the aberration generated in the subject's eye is polarization-dependent.

Third Embodiment

Figure 5:
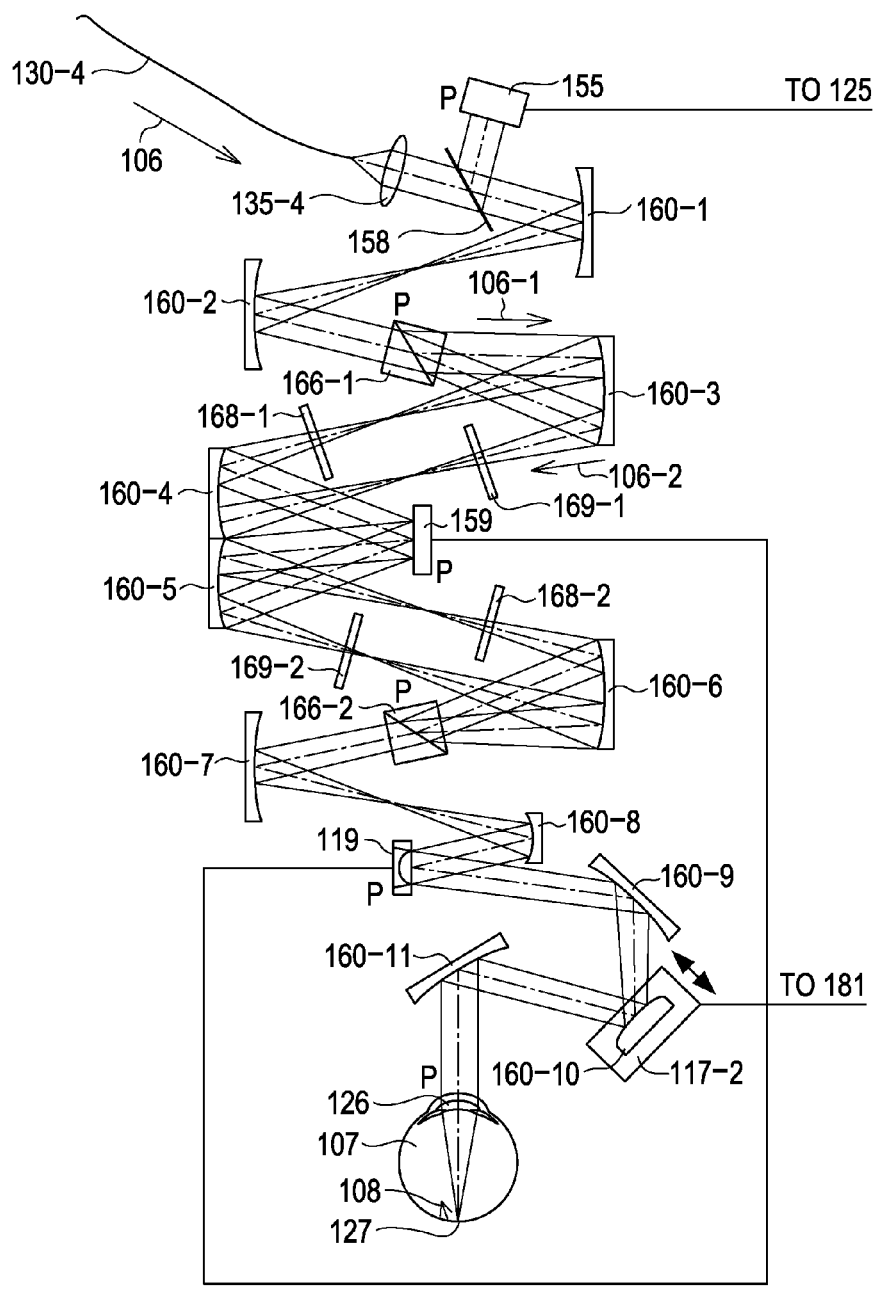
FIG. 5 illustrates an OCT apparatus using one spatial unit according to a third embodiment of the present invention.

An OCT apparatus according to a third embodiment, in which one reflective spatial light modulator employing the orientation of liquid crystal is used to correct the aberration, will be described. As described above, in the first and second embodiments, two spatial light modulators respectively modulate the p-polarized light and the s-polarized light so as to correct the aberration. In contrast, as illustrated in FIG. 5, in the third embodiment, one spatial light modulator is used and one of the polarized beams is rotated so that the polarization is aligned, whereby modulation can be performed irrespective of the polarization state of the measuring beam or the return beam. Thus, the third embodiment is characterized by the optical path of the measuring beam. Because the structures of the light source, the reference optical path, the measurement system are the same as those of the first embodiment, the description of these are omitted, and the structure of the optical path of the measuring beam will be mainly described. In FIG. 5, the optical fiber 130-4, the lens 135-4, the beam splitter 158, the spherical mirrors 160-1 to 160-11, a first Wollaston prism 166-1, and a second Wollaston prism 166-2 are illustrated. A first half-wavelength plate 168-1, a second half-wavelength plate 168-2, a first optical path compensating plate 169-1, a second optical path compensating plate 169-2, and a reflective spatial light modulator 159 employing the orientation of liquid crystal are drawn.

In the third embodiment, the measuring beam 106 is split by the first Wollaston prism 166-1 into the first measuring beam 106-1 composed of an s-polarized light (perpendicular to the paper surface of FIG. 5) and the second measuring beam 106-2 composed of a p-polarized light (parallel to the paper surface of FIG. 5). The polarization direction of the first measuring beam 106-1 composed of the s-polarized light is rotated by 90° by the first half-wavelength plate 168-1. Thus, the polarization direction of the first measuring beam 106-1 is aligned with the polarization direction of the second measuring beam 106-2 composed of the p-polarized light, and the first measuring beam 106-1 and the second measuring beam 106-2 impinge on the spatial light modulator 159 at the same position, so that modulation can be performed irrespective of the polarization states of the measuring beams. The first optical path compensating plate 169-1 and the second optical path compensating plate 169-2 respectively compensate the first half-wavelength plate and the 168-1 and the second half-wavelength plate 168-2 for the optical path length or the deviation. After entering the subject's eye 107, the measuring beam 106 is reflected by the retina 127 or scattered to become the return beam 108, is guided again to the optical coupler 131, and reaches the line sensor 139. The return beam 108 is split into s-polarized light and p-polarized light by the second Wollaston prism 166-2. The polarization direction of one of the polarized beams that have been split is rotated by 90° by the second half-wavelength plate 168-2, so that the polarized beams are modulated by the spatial light modulator 159 irrespective of the polarization state, and then combined by the first Wollaston prism 166-1.

A part of the return beam 108, which is split by the beam splitter 158, enters the wavefront sensor 155, and the aberration of the return beam 108 is measured. The wavefront sensor 155 is electrically connected to the personal computer 125. Here, the spherical mirrors 160-1 to 160-9 are disposed so that the cornea 126, the XY scanner 119, the wavefront sensor 155, the spatial light modulator 159, and the beam-splitting surface of the Wollaston prisms 166-1 and 166-2 are optically conjugate to each other. The positions that are conjugate to each other are denoted by "P". Therefore, the wavefront sensor 155 can measure the aberration of the subject's eye 107. The aberration of the subject's eye 107 can be corrected on the basis of the aberration measured by the wavefront sensor 155. That is, the spatial light modulator 159 is controlled in real time on the basis of the aberration that is measured, so that the aberration generated in the subject's eye 107 is corrected and a tomographic image having a higher horizontal resolution can be acquired. The descriptions of the method and the steps of acquiring a tomographic image, which are the same as those of the first embodiment, are omitted.

As described above, according to the third embodiment, irrespective of the polarization state, the measuring beam or the return beam can be modulated by using one spatial light modulator so as to correct the aberration. As a result, the signal to noise ratio of the tomographic image can be increased.

Fourth Embodiment

An OCT apparatus according to a fourth embodiment of the present invention will be described. In particular, an OCT apparatus including an adaptive optics system that acquires a tomographic image (OCT image) of a subject's eye with high horizontal resolution will be described. The fourth embodiment, which is similar to the second embodiment, is a Fourier domain OCT apparatus that acquires a tomographic image of a subject's eye by correcting the aberration of the subject's eye by using two reflective spatial light modulators. Using the OCT apparatus a good tomographic image can be acquired irrespective of the diopter or the aberration of the subject's eye. Such an OCT apparatus can acquire a good tomographic image irrespective of the diopter or the aberration the subject's eye. Here, in addition to the structure that same as that of the second embodiment, modulation is performed on the measuring beam or the return beam after correcting the distortion of two spatial light modulators. Here, the term "distortion" refers to the distortion of the reflection surface of a reflective spatial light modulator. The two spatial light modulators are disposed so as to optimize the diffraction efficiency of the spatial light modulators. The fourth embodiment is characterized by the measuring optical path and the method of driving the spatial light modulator. The structures of the light source, the reference optical path, the measurement system, and the method of acquiring a tomographic image are basically the same as those of the second embodiment. Therefore, the description of these are omitted, and the measuring optical path and the method of driving the spatial light modulator will be mainly described.

Figure 6A:
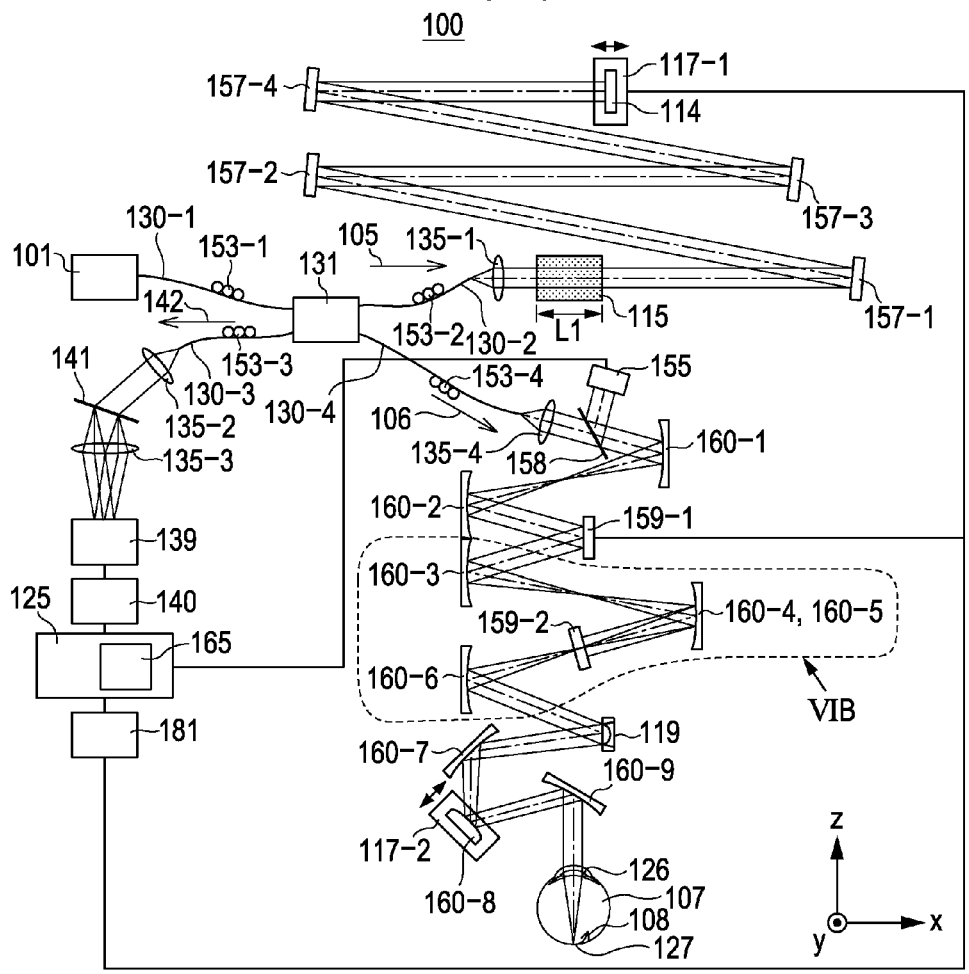
FIGS. 6A and 6B illustrate the overall structure of an OCT apparatus according to a fourth embodiment of the present invention.
Figure 6B:
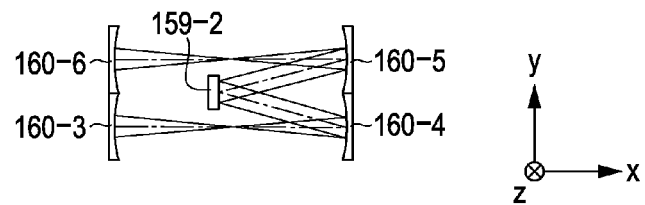

First, referring to FIGS. 6A and 6B, the overall structure of the optical system of the OCT apparatus according to the fourth embodiment will be described. In FIGS. 6A and 6B, the elements the same as those of FIG. 4 are denoted by the same numerals, and redundant description will be omitted. FIG. 6A is a plan view of the OCT apparatus parallel to the XZ-plane, and FIG. 6B is a partial plan view parallel to the XY-plane. The aberration of the return beam 108 is measured by the wavefront sensor 155. Here, the two spatial light modulators 159-1 and 159-2, which are optically serially disposed, are controlled so as to reduce the aberration, so that a good tomographic image can be obtained irrespective of the diopter or the aberration of the subject's eye.

Next, the optical path of the measuring beam 106, which characterizes the fourth embodiment, will be described. The measuring beam 106 passes through the beam splitter 158, is reflected by the spherical mirrors 160-1 and 160-2, and enters the first spatial light modulator 159-1. Here, the first spatial light modulator 159-1 is oriented so as to modulate the phase of p-polarized light (parallel to the XZ-plane direction). Next, the measuring beam 106 is modulated by the first spatial light modulator 159-1, reflected by the spherical mirror 160-3, reflected by the spherical mirror 160-4 in the +Y direction, and enters the second spatial light modulator 159-2. Here, the second spatial light modulator 159-2 is oriented so as to modulate the phase of p-polarized light (parallel to the XY-plane direction). Here, both of the two spatial light modulator 159-1 and 159-2 modulate p-polarized beams having the polarization direction that are perpendicular to each other. The orientation of liquid crystal of the spatial light modulator is aligned with the incident direction of the measuring beam 106 or the return beam 108 so as to modulate p-polarized light, whereby the diffraction efficiency is optimized. That is, the spherical mirror 160-4 is disposed so that the plane defined by the incoming optical path to the first spatial light modulator 159-1 (the optical axis, to be precise) and the outgoing optical path from the first optical modulator 159-1 and a plane that is defined by the incoming optical path to the second spatial light modulator 159-2 and the outgoing optical path from the second spatial light modulator 159-2 are perpendicular to each other. Thus, the modulation described above is realized.

The spatial light modulators 159-1 and 159-2 each modulate a polarization component having a specific polarization direction by employing the orientation of liquid crystal. Therefore, as described above, the fourth embodiment can modulate all polarization components of the measuring beam 106 by continuously performing modulation on the polarization component that is parallel to the XZ-plane and the polarization component that is parallel to the XY-plane. Next, the measuring beam 106 is guided by the second spatial light modulator 159-2 to the +Y direction, reflected by the spherical mirrors 160-5 and 160-6, and enters the mirror of the XY scanner 119. The polarization component in the XY-plane direction and the polarization component in the XZ-plane direction of the return beam 108 are respectively modulated again by the second spatial light modulator 159-2 and the first spatial light modulator 159-1. A part of the return beam 108, which is split from the return beam 108 by the beam splitter 158, enters the wavefront sensor (aberration measuring unit) 155 that measures the aberration of the return beam 108.

Next, the method of driving the spatial light modulator will be described. In general, the reflection surface of a reflective spatial light modulator has a distortion of, for example, about 1 μm. Therefore, the measuring beam 106 that enters the subject's eye 107 has aberration that is generated due to the distortions of the spatial light modulators 159-1 and 159-2. The spatial light modulators 159-1 and 159-2 can correct the aberration generated due to the distortion, as long as distortion is included in the polarization component that can be modulated by the spatial light modulators 159-1 and 159-2. To be specific, a modulation amount for correcting the distortion of the reflection surface, which has been measured beforehand, is input to the spatial light modulator, so that the reflection surface can be regarded as optically flat with respect to a corresponding polarization component. The data for the modulation amounts for correcting the distortions of the reflection surfaces of the spatial light modulators 159-1 and 159-2 are stored as a database 165 in the memory of the personal computer 125. The modulation amount output to the spatial light modulators 159-1 and 159-2 can be calculated by using the data for the modulation amounts. Moreover, as described above, the spatial light modulator 159-1 is oriented so as to modulate the polarization component in the XZ-plane direction and the spatial light modulator 159-2 is oriented so as to modulate the polarization component in the XY-plane direction. Therefore, among the polarization components of the aberration generated by the distortions of the spatial light modulators 159-1 and 159-2, the polarization component in the XZ-plane direction can be corrected by the spatial light modulator 159-1, and the polarization component in the XY-plane direction can be corrected by the spatial light modulator 159-2.

To be specific, the correction can be performed by inputting a modulation amount (S1+S2) to each of the spatial light modulators 159-1 and 159-2, where S1 denotes the modulation amount for correcting the distortion of the spatial light modulator 159-1 and S2 denotes the modulation amount for correcting the distortion of the spatial light modulator 159-2. With consideration of the thickness and unevenness of the liquid crystal layer of the spatial light modulator, a value generated by correcting (S1+S2) may be input as a modulation amount. This is because, regarding the polarized beam in the XZ-plane direction, the aberration generated due to the distortions of the spatial light modulators 159-1 and 159-2 can be corrected by the spatial light modulator 159-1. Likewise, regarding the polarized beam in the XY-plane direction, the aberration generated due to the distortions of the spatial light modulators 159-1 and 159-2 can be corrected by the spatial light modulator 159-2. Thus, the aberration generated due to the distortions of the spatial light modulators 159-1 and 159-2 can be corrected, so that the measuring beam 106 in which the aberration generated due to the distortions of the spatial light modulators 159-1 and 159-2 can be made to enter the subject's eye 107. Likewise, the aberration of the return beam 108 due to the distortions of the spatial light modulators 159-1 and 159-2 can be corrected.

Figure 7:
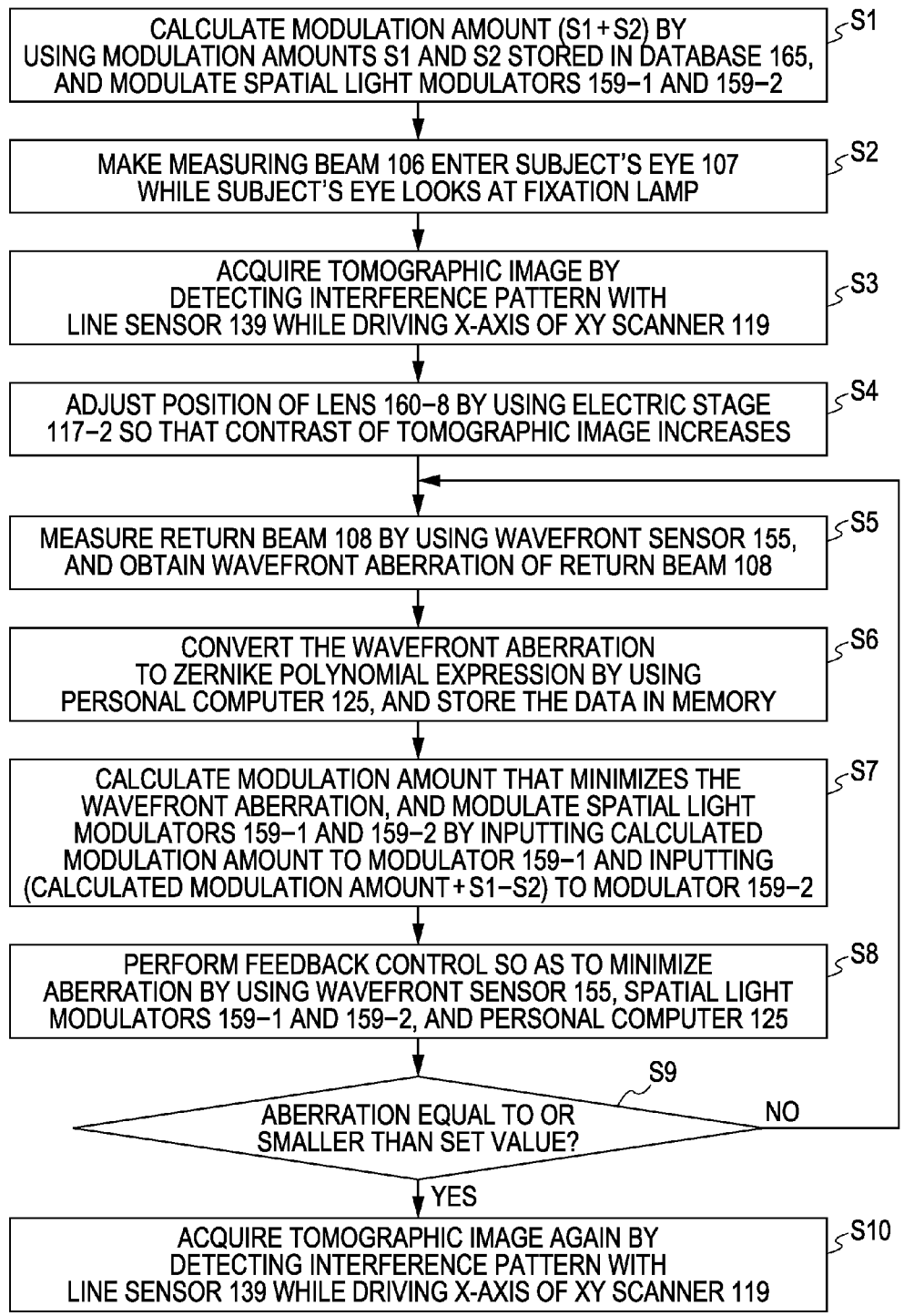
FIG. 7 is a flowchart illustrating steps of acquiring a tomographic image by using the OCT apparatus according to the fourth embodiment of the present invention.

Next, referring to FIGS. 6A to 7, the steps of acquiring a tomographic image by using the OCT apparatus will be described. FIG. 7 is a flowchart illustrating the steps of acquiring a tomographic image by using the OCT apparatus 100 according to the fourth embodiment of the present invention. Here, as illustrated in FIGS. 6A and 6B, an aberration generated by the subject's eye 107 having myopia and astigmatism is corrected by using the two spatial light modulators 159-1 and 159-2 so as to acquire a high-horizontal-resolution tomographic image of the retina 127. The OCT apparatus 100 is configured so that the influence of the aberration generated due to the distortions of the two spatial light modulators 159-1 and 159-2 can be reduced.

The tomographic image is acquired by performing the following steps (1) to (10). The steps may be performed sequentially or in a different order. The steps may be automatically performed by using a computer. FIG. 7 is a flowchart of the process of acquiring the tomographic image.

(1) In step 1 (S1 in FIG. 7), by using the modulation amounts S1 and S2 for correcting the distortions of the spatial light modulators 159-1 and 159-2, which are stored beforehand in the database 165 of the personal computer 125, the modulation amount (S1+S2) is calculated, and the spatial light modulators 159-1 and 159-2 are modulated.

(2) In step 2 (S2 in FIG. 7), the measuring beam 106 is made to enter the subject's eye 107 while subject's eye looks at a fixation lamp (not shown). Here, the position of the spherical mirror 160-8 is adjusted by the electric stage 117-2 so that the measuring beam 106 enters the subject's eye 107 as a collimated beam.

(3) In step 3 (S3 in FIG. 7), a tomographic image (not shown) is acquired by detecting an interference pattern with the line sensor 139 while driving the X-axis of the XY scanner 119.

(4) In step 4 (S4 in FIG. 7), where performing step 2, the position of the spherical mirror 160-8 is adjusted by using the electric stage 117-2 so that the contrast of the tomographic image increases.

(5) In step 5 (S5 in FIG. 7), the return beam 108 is measured by using the wavefront sensor 155, and the aberration of the return beam 108 is acquired. In particular, the aberration acquired in this step includes the distortions of the spatial light modulators 159-1 and 159-2.

(6) In step 6 (S6 in FIG. 7), the acquired aberration is converted to a Zernike polynomial expression by using the personal computer 125, and the data is stored in a memory.

(7) In step 7 (S7 in FIG. 7), the modulation amount that minimizes the acquired aberration is calculated, and the spatial light modulators 159-1 to 159-2 are modulated. Here, because the first spatial light modulator 159-1 and the second spatial light modulator 159-2 are optically conjugate to each other, the same modulation amount is input. Alternatively, with consideration of the thickness and unevenness of the liquid crystal layer of the spatial light modulators, a value generated by correcting the modulation amount may be input. The aberration acquired in step 5 includes the distortions of the spatial light modulators 159-1 and 159-2, the aberration generated due to the distortions are corrected here.

(8) In step 8 (S8 in FIG. 7), feedback control is performed so as to minimize the aberration by using the wavefront sensor 155, spatial light modulators 159-1 and 159-2, the personal computer 125, and the spatial light modulator driver 18 so as to control the spatial light modulators 159-1 and 159-2 in real time. Here, the input to the spatial light modulator 159-2 is performed in the same manner as step 7.

(9) In step 9 (S9 in FIG. 7), whether the aberration is equal to or smaller than a set value is determined, and steps 5 to 8 are repeated until the aberration converges. The set value can be about 0.1 μm (RMS).

(10) In step 10 (S10 in FIG. 7), while driving the X-axis of the XY scanner 119, an interference pattern is detected by the line sensor 139 and the tomographic image is acquired again.

As described above, according to the fourth embodiment, the aberration of the measuring beam or the return beam generated due to the distortions of the two spatial light modulators is reduced, so that the aberration can be corrected with a higher precision. As a result, the signal to noise ratio of a tomographic image can be increased. The aberration of the measuring beam or the return beam that is generated due to the distortions of the first spatial light modulator and the second spatial light modulator is corrected for each polarization component, so that the distortions of the first spatial light modulator and the second spatial light modulator can be corrected. As a result, the signal to noise ratio of a tomographic image can be increased. The modulation amount that is input to the spatial light modulator is calculated on the basis of the data for the modulation amount for optically correcting the distortions of the spatial light modulator, so that the distortion of the spatial light modulator can be optically corrected. As a result, a high resolution tomographic image can be acquired. A database containing data for the modulation amount for optically correcting the distortion of the spatial light modulator is provided, so that the distortion of the spatial light modulator can be optically corrected easily. As a result, a high resolution tomographic image can be easily acquired. The sum of the first modulation amount and the second modulation amount is used, so that the distortion of the spatial light modulator can be corrected for each polarization component. As a result, a high resolution tomographic image can be acquired. On the optical path of the measuring beam or the return beam, a plane including the incoming optical path to the first spatial light modulator and the outgoing optical path from the first spatial light modulator and a plane that includes the incoming optical path to the second spatial light modulator and the outgoing optical path from the second spatial light modulator can be made to be perpendicular to each other. Thus, the p-polarization component of the measuring beam or the return beam can be made to be modulated by the two spatial light modulators. As a result, the diffraction efficiency of the spatial light modulator is optimized and the signal to noise ratio of a tomographic image can be increased.

Other Embodiments

Aspects of the present invention can also be realized by a computer of a system or apparatus (or devices such as a CPU or MPU) that reads out and executes a program recorded on a memory device to perform the functions of the above-described embodiments, and by a method, the steps of which are performed by a computer of a system or apparatus by, for example, reading out and executing a program recorded on a memory device to perform the functions of the above-described embodiments. For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-244948 filed Oct. 23, 2009, and No. 2010-030919 filed Feb. 16, 2010, which are hereby incorporated by reference herein in their entirety.

What is claimed is:
1. An adaptive optics apparatus comprising:
a first spatial light modulation unit configured to modulate the phase of one of two polarization components of light and disposed at a position that is optically conjugate to an object;

a second spatial light modulation unit configured to modulate the phase of the other of the two polarization components and disposed at a position that is optically conjugate to the object; and an irradiation unit configured to irradiate the object with light that has the modulated phase of the two polarization components by the first and second spatial light modulation units.

2. The adaptive optics apparatus according to claim 1, further comprising:

an aberration measuring unit configured to measure an aberration of the object and disposed at a position that is optically conjugate to the first and second spatial light modulation units, wherein the first and second spatial light modulation units are configured to modulate the phases of the two polarization components on the basis of a measurement result obtained by the aberration measuring unit.

3. The adaptive optics apparatus according to claim 1, wherein the object is a subject's eye, and wherein the first and second spatial light modulation units are disposed at a position that is optically conjugate to an anterior ocular segment of the subject's eye.

4. The adaptive optics apparatus according to claim 1, wherein each of the first and second spatial light modulation units is configured to modulate each of two polarization components of a return beam at a position that is optically conjugate to the object, the return beam returning from the object that is irradiated with light by the irradiation unit.

5. The adaptive optics apparatus according to claim 1, wherein the first and second spatial light modulation units are optically parallel disposed or optically serially disposed.

6. An imaging apparatus comprising:

the adaptive optics apparatus according to claim 1; and an image acquiring unit configured to acquire an image of the object on the basis of a return beam that returns from the object when the object is irradiated with light by the irradiation unit.

7. The imaging apparatus according to claim 6, further comprising:

a splitting unit configured to split the light emitted by a light source into a beam that enters the first and second spatial light modulation units and a reference beam, wherein the image acquiring unit acquires a tomographic image of the object on the basis of an interference beam that is generated by interference between a return beam and the reference beam.

8. The imaging apparatus according to claim 6, wherein light that is used by the aberration measuring unit to measure the aberration and light that is used to acquire an image of the object are emitted by light sources that are different from each other.

9. The adaptive optics apparatus according to claim 1, wherein the first and second spatial light modulation units are liquid crystals, and wherein orientations of the liquid crystals intersect with each other.

10. The adaptive optics apparatus according to claim 1, wherein the first spatial light modulation unit is disposed so as to modulate the phrase of p-polarized light, and wherein the second spatial light modulation unit is disposed so as to modulate the phase of s-polarized light.

11. The adaptive optics apparatus according to claim 10, further comprising:

a polarizing light splitting unit configured to split the light emitted by the light source into the p-polarized and the s-polarized light, and a combining unit configured to combine the p-polarized light via the first spatial light modulation unit and the s-polarized light via the second spatial light modulation unit.

12. The adaptive optics apparatus according to claim 1, further comprising:

a driving unit configured to drive the first and second spatial light modulation units so as to correct distortions of surfaces of the first and second spatial light modulation units.

13. An imaging apparatus comprising:

the adaptive optics apparatus according to claim 3; and an image acquiring unit configured to acquire an image of a fundus of the subject's eye on the basis of a return beam that returns from the fundus irradiated with light from the first and second spatial light modulation units.

14. An adaptive optics method comprising:

modulating the phase of one of two polarization components of light at a position that is optically conjugate to an object;

modulating the phase of the other of the two polarization components at the position that is optically conjugate to the object; and irradiating the object with light that has the modulated phase of the two polarization components.

15. A non-transitory computer-readable storage medium storing a program for causing a computer to execute a method for an adaptive optics apparatus, the method comprising:

modulating the phase of one of two polarization components of light at a position that is optically conjugate to an object;

modulating the phase of the other of the two polarization components at the position that is optically conjugate to the object; and irradiating the object with light that has the modulated phase of the two polarization components.

16. An adaptive optics apparatus comprising:

a first spatial light modulation unit configured to modulate the phase of one of two polarization components of light and disposed at a position that is optically conjugate to an object;

a second spatial light modulation unit configured to modulate the phase of the other of the two polarization components and disposed at a position that is optically conjugate to the object; and a scanning unit configured to scan, in the object, light that has the modulated phase of the two polarization components by the first and second spatial light modulation units, wherein the scanning unit is disposed at a position that is optically conjugate to the first and second spatial light modulation units.

17. The adaptive optics apparatus according to claim 16, wherein the object is a subject's eye, and wherein the first and second spatial light modulation units are disposed at a position that is optically conjugate to an anterior ocular segment of the subject's eye.

18. An imaging apparatus comprising:

the adaptive optics apparatus according to claim 17; and an image acquiring unit configured to acquire an image of a fundus of the subject's eye on the basis of a return beam that returns from the fundus irradiated with light from the first and second spatial light modulation units.

19. The adaptive optics apparatus according to claim 16, wherein the first and second spatial light modulation units are optically parallel disposed or optically serially disposed.

20. The adaptive optics apparatus according to claim 16, further comprising:
a driving unit configured to drive the first and second spatial light modulation units so as to correct distortions of surfaces of the first and second spatial light modulation units.

21. An imaging apparatus comprising:
adaptive optics apparatus according to claim 16; and
an image acquiring unit configured to acquire an image of the object on the basis of a return beam that returns from the object irradiated with light from the first and second spatial light modulation units.

22. The adaptive optics apparatus according to claim 16, further comprising:
an aberration measuring unit configured to measure an aberration of the object and disposed at a position that is optically conjugate to the first and second spatial light modulation units,
wherein the first and second spatial light modulation units are configured to modulate the phases of the two polarization components on the basis of a measurement result obtained by the aberration measuring unit.

23. An adaptive optics apparatus comprising:
a polarizing light splitting unit configured to split light emitted by a light source into p- polarized light and s-polarized light;
a first spatial light modulation unit configured to modulate the phase of p-polarized light and disposed at a position that is optically conjugate to an object;
a second spatial light modulation unit configured to modulate the phase of s-polarized light and disposed at a position that is optically conjugate to the object; and
a polarizing light combining unit configured to combine the p-polarized light via the first spatial light modulation unit and the s-polarized light via the second spatial light modulation unit.

24. The adaptive optics apparatus according to claim 23, wherein the object is a subject's eye, and
wherein the first and second spatial light modulation units are disposed at a position that is optically conjugate to an anterior ocular segment of the subject's eye.

25. An imaging apparatus comprising:
the adaptive optics apparatus according to claim 24; and
an image acquiring unit configured to acquire an image of a fundus of the subject's eye on the basis of a return beam that returns from the fundus irradiated with light from the first and second spatial light modulation units.

26. The adaptive optics apparatus according to claim 23, wherein the first and second spatial light modulation units are optically parallel disposed or optically serially disposed.

27. The adaptive optics apparatus according to claim 23, further comprising:
a driving unit configured to drive the first and second spatial light modulation units so as to correct distortions of surfaces of the first and second spatial light modulation units.

28. An imaging apparatus comprising:
adaptive optics apparatus according to claim 23; and
an image acquiring unit configured to acquire an image of the object on the basis of a return beam that returns from the object irradiated with light from the first and second spatial light modulation units.

29. The adaptive optics apparatus according to claim 23, further comprising:
an aberration measuring unit configured to measure an aberration of the object and disposed at a position that is optically conjugate to the first and second spatial light modulation units,
wherein the first and second spatial light modulation units are configured to modulate the phases of the two polarization components on the basis of a measurement result obtained by the aberration measuring unit.

30. An adaptive optics apparatus comprising:
a first spatial light modulation unit configured to modulate the phase of one of two polarization components of light and disposed at a position that is optically conjugate to an object;
a second spatial light modulation unit configured to modulate the phase of the other of the two polarization components and disposed at a position that is optically conjugate to the object; and
a plurality of reflective optical members disposed so that the first spatial light modulation means is disposed at a position that is optically conjugate to the second spatial light modulation means.

31. The adaptive optics apparatus according to claim 30, wherein at least one of the plurality of reflective optical members is a spherical mirror.

32. The adaptive optics apparatus according to claim 30, wherein the object is a subject's eye, and
wherein the first and second spatial light modulation units are disposed at a position that is optically conjugate to an anterior ocular segment of the subject's eye.

33. An imaging apparatus comprising:
the adaptive optics apparatus according to claim 32; and
an image acquiring unit configured to acquire an image of a fundus of the subject's eye on the basis of a return beam that returns from the fundus irradiated with light from the first and second spatial light modulation units.

34. The adaptive optics apparatus according to claim 30, wherein the first and second spatial light modulation units are optically parallel disposed or optically serially disposed.

35. The adaptive optics apparatus according to claim 30, further comprising:
a driving unit configured to drive the first and second spatial light modulation units so as to correct distortions of surfaces of the first and second spatial light modulation units.

36. An imaging apparatus comprising:
adaptive optics apparatus according to claim 30; and
an image acquiring unit configured to acquire an image of the object on the basis of a return beam that returns from the object irradiated with light from the first and second spatial light modulation units.

37. The adaptive optics apparatus according to claim 30, further comprising:
an aberration measuring unit configured to measure an aberration of the object and disposed at a position that is optically conjugate to the first and second spatial light modulation units,
wherein the first and second spatial light modulation units are configured to modulate the phases of the two polarization components on the basis of a measurement result obtained by the aberration measuring unit.

38. An adaptive optics apparatus comprising:
a first spatial light modulation unit configured to modulate the phase of one of two polarization components of light and disposed at a position that is optically conjugate to an object; and
a second spatial light modulation unit configured to modulate the phase of the other of the two polarization components and disposed at a position that is optically conjugate to the object.

39. The adaptive optics apparatus according to claim 31, wherein the object is a subject's eye, and
wherein the first and second spatial light modulation units are disposed at a position that is optically conjugate to an anterior ocular segment of the subject's eye.

40. An imaging apparatus comprising:
adaptive optics apparatus according to claim 39; and
an image acquiring unit configured to acquire an image of a fundus of the subject's eye on the basis of a return beam that returns from the fundus irradiated with light from the first and second spatial light modulation units.

41. The adaptive optics apparatus according to claim 38, wherein the first and second spatial light modulation units are optically parallel disposed or optically serially disposed.

42. The adaptive optics apparatus according to claim 38, further comprising:
a driving unit configured to drive the first and second spatial light modulation units so as to correct distortions of surfaces of the first and second spatial light modulation units.

43. An imaging apparatus comprising:
adaptive optics apparatus according to claim 38; and
an image acquiring unit configured to acquire an image of the object on the basis of a return beam that returns from the object irradiated with light from the first and second spatial light modulation units.

44. The adaptive optics apparatus according to claim 38, further comprising:
an aberration measuring unit configured to measure an aberration of the object and disposed at a position that is optically conjugate to the first and second spatial light modulation units,
wherein the first and second spatial light modulation units are configured to modulate the phases of the two polarization components on the basis of a measurement result obtained by the aberration measuring unit.

45. An adaptive optics apparatus comprising:
an irradiation unit configured to irradiate an object with measurement light;
a first spatial light modulation unit configured to modulate a phase of one of two polarization components included in a return beam that returns from the object irradiated with the measurement light and disposed at a position that is optically approximately conjugate to the object in an optical path of the return beam; and
a second spatial light modulation unit configured to modulate a phase of an other of the two polarization components and disposed at a position that is optically approximately conjugate to the object in the optical path of the return beam.

46. The adaptive optics apparatus according to claim 45, wherein the object is a subject's eye, and
wherein the first and second spatial light modulation units are disposed at a position that is optically conjugate to an anterior ocular segment of the subject's eye.

47. An imaging apparatus comprising:
adaptive optics apparatus according to claim 46; and
an image acquiring unit configured to acquire an image of a fundus of the subject's eye on the basis of a return beam that returns from the fundus irradiated with light from the first and second spatial light modulation units.

48. The adaptive optics apparatus according to claim 45, wherein the first and second spatial light modulation units are optically parallel disposed or optically serially disposed.

49. An imaging apparatus comprising:
the adaptive optics apparatus according to claim 45; and
an image acquiring unit configured to acquire an image of the object on the basis of a return beam that returns from the object irradiated with light from the first and second spatial light modulation units.

50. The adaptive optics apparatus according to claim 45, further comprising:
a driving unit configured to drive the first and second spatial light modulation units so as to correct distortions of surfaces of the first and second spatial light modulation units.

51. The adaptive optics apparatus according to claim 45, further comprising:
an aberration measuring unit configured to measure an aberration of the object and disposed at a position that is optically conjugate to the first and second spatial light modulation units,
wherein the first and second spatial light modulation units are configured to modulate the phases of the two polarization components on the basis of a measurement result obtained by the aberration measuring unit.

* * * * *